United States Patent
Chang et al.

(10) Patent No.: US 9,254,255 B2
(45) Date of Patent: Feb. 9, 2016

(54) DENTAL CARE PRODUCT WITH TWO-PART FORMULATIONS AND UTILITY THEREOF

(71) Applicant: CHUNG-YUAN CHRISTIAN UNIVERSITY, Tao-Yuan (TW)

(72) Inventors: Yung Chang, Tao-Yuan (TW); Yu-Ju Shih, Tao-Yuan (TW); Bor-Shiunn Lee, Tao-Yuan (TW); Da-Ming Wang, Tao-Yuan (TW); Juin-Yih Lai, Tao-Yuan (TW)

(73) Assignee: CHUNG-YUAN CHRISTIAN UNIVERSITY, Tao-Yuan (TW)

( * ) Notice: Subject to any disclaimer, the term of this patent is extended or adjusted under 35 U.S.C. 154(b) by 0 days.

(21) Appl. No.: 14/604,058

(22) Filed: Jan. 23, 2015

(65) Prior Publication Data
US 2015/0150781 A1 Jun. 4, 2015

Related U.S. Application Data

(63) Continuation of application No. 12/953,036, filed on Nov. 23, 2010, now Pat. No. 8,980,232.

(51) Int. Cl.
*A61K 8/90* (2006.01)
*A61Q 11/00* (2006.01)
*A01N 41/08* (2006.01)

(52) U.S. Cl.
CPC . *A61K 8/90* (2013.01); *A01N 41/08* (2013.01); *A61Q 11/00* (2013.01); *A61K 2800/5424* (2013.01); *A61K 2800/5426* (2013.01); *A61K 2800/5428* (2013.01); *A61K 2800/594* (2013.01); *A61K 2800/884* (2013.01)

(58) Field of Classification Search
USPC .......................................... 424/54, 78.17, 489
See application file for complete search history.

(56) References Cited

U.S. PATENT DOCUMENTS

| 6,117,417 | A | 9/2000 | Wicks et al. |
| 2005/0287111 | A1 | 12/2005 | Schlenoff et al. |
| 2008/0181861 | A1 | 7/2008 | Jiang et al. |

*Primary Examiner* — Walter Webb
(74) *Attorney, Agent, or Firm* — WPAT, PC; Justin King (57) ABSTRACT

A dental care product comprises an orally acceptable carrier or excipient, and a bacterial resistance copolymer, which comprises a zwitterionic block and a charged anchoring block, wherein the anchoring block binds to tooth surfaces by electrostatic attraction, and the zwitterionic block extends outwardly to reduce the attachment of bacteria to tooth surfaces.

15 Claims, 12 Drawing Sheets

DENTAL CARE PRODUCT WITH TWO-PART FORMULATIONS AND UTILITY THEREOF

CROSS-REFERENCE TO RELATED APPLICATIONS

This application is a continuing application of and claims priority benefit of application Ser. No. 12/953,036, filed on Nov. 23, 2010, now pending, the entirety of the above-mentioned patent application is incorporated herein by reference and a part of this specification.

BACKGROUND OF THE INVENTION

1. Field of the Invention

The present invention relates to dental care products with two-part formulations and utility thereof.

2. Description of the Prior Art

Most people suffer from dental caries. The causation of dental caries may include several factors. It is generally believed that dental plaque contributes significant to tooth decay. Dental plaque is usually a colorless biofilm naturally developed by colonizing bacteria and depositing salivary proteins and food debris on a tooth, and it can lead to dental calculus, gingivitis, and other related gum diseases. Moreover, in plaque, *Streptococcus mutans* converts sugar into organic acids, which release hydrogen ions in the subsurface layers of enamel, causing that the enamel diffuses calcium and phosphate ions out of the enamel and thus cavities are developed.

Dental care products, such as mouthwash, toothpaste, and dentifrice, have been used over one hundred years for eliminating malodor and killing bacteria of the oral cavity. Essential oils such as thymol, methyl salicylate, menthol, and eucalyptol, are active ingredients in antiseptic, mouthwashes such as Listerine®. In addition, mouthwashes usually contain alcohol as solvent of the active ingredients, and contain surfactants to solubilize the essential oils and/or other compositions. Moreover, other effective antimicrobial agents, such as cetyl pyridinum chloride (CPC), chlorhexidine gluconate, hydrogen peroxide, benzoic acid, phenolic compounds, and fluorides may also be employed as active ingredients.

It has been found that the efficacy of many active ingredients is reduced due to the presence of surfactants, and many ingredients are considered unsafe for human use. Therefore, it would be advantageous to develop safer and more effective dental care products.

SUMMARY OF THE INVENTION

The present invention relates dental care products with high degree of bacterial resistance.

One embodiment of the present invention provides a dental care product, comprising: an orally acceptable carrier or excipient; and equal to or more than 0.1 mg/ml of a first bacterial resistance copolymer, with a zwitterionic block and an anchoring block with a first electricity, wherein the anchoring block binds to tooth surfaces by electrostatic attraction, and the zwitterionic block extends outwardly to reduce the attachment of bacteria to tooth surfaces.

Another embodiment of the present invention provides a dental care product with two-part formulations, comprising a first agent and a second agent. The first agent includes: an orally acceptable first carrier or excipient; and equal to or more than 0.1 mg/ml of a first bacterial resistance copolymer, with a first zwitterionic block and a first anchoring block with a first electricity, wherein the first anchoring block binds to tooth surfaces by electrostatic attraction, and the first zwitterionic block extends outwardly to reduce the attachment of bacteria to tooth surfaces. The second agent includes: an orally acceptable second carrier or excipient; and equal to or more than 0.1 mg/ml of a second bacterial resistance copolymer, with a second zwitterionic block and a second anchoring block with a second electricity opposite to the first electricity, wherein the anchoring block binds to tooth surfaces by electrostatic attraction, and the zwitterionic block extends outwardly to reduce the attachment of bacteria to tooth surfaces.

DESCRIPTION OF THE PREFERRED EMBODIMENT

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a through understanding of the present invention. The present invention may be practiced without some or all of these specific details. In other instances, well-known process operations and components are not been described in detail in order not to unnecessarily obscure the present invention. While drawings are illustrated in details, it is appreciated that the quantity of the disclosed components may be greater or less than that disclosed, except expressly restricting the amount of the components.

Oral bacteria is responsible for oral malodor, dental calculus, dental plaque, and the resulting tooth and gum diseases. Conventional dental care products employ essential oils or antibacterial agents for killing bacteria. Different from the prior art, the present invention provides dental care products having an ultra high degree of bacterial resistance towards oral bacteria, and it has surprisingly found that conventional antibacterial agents or essential oils may be unnecessary. In addition, the dental care products of the embodiments of this invention are safe for human use.

One embodiment of the present invention provides a dental care product that at least includes an orally acceptable carrier or excipient and equal to or more than 0.1 mg/ml of a bacterial resistance copolymer; the copolymer is used as the active ingredient.

Figure 1:
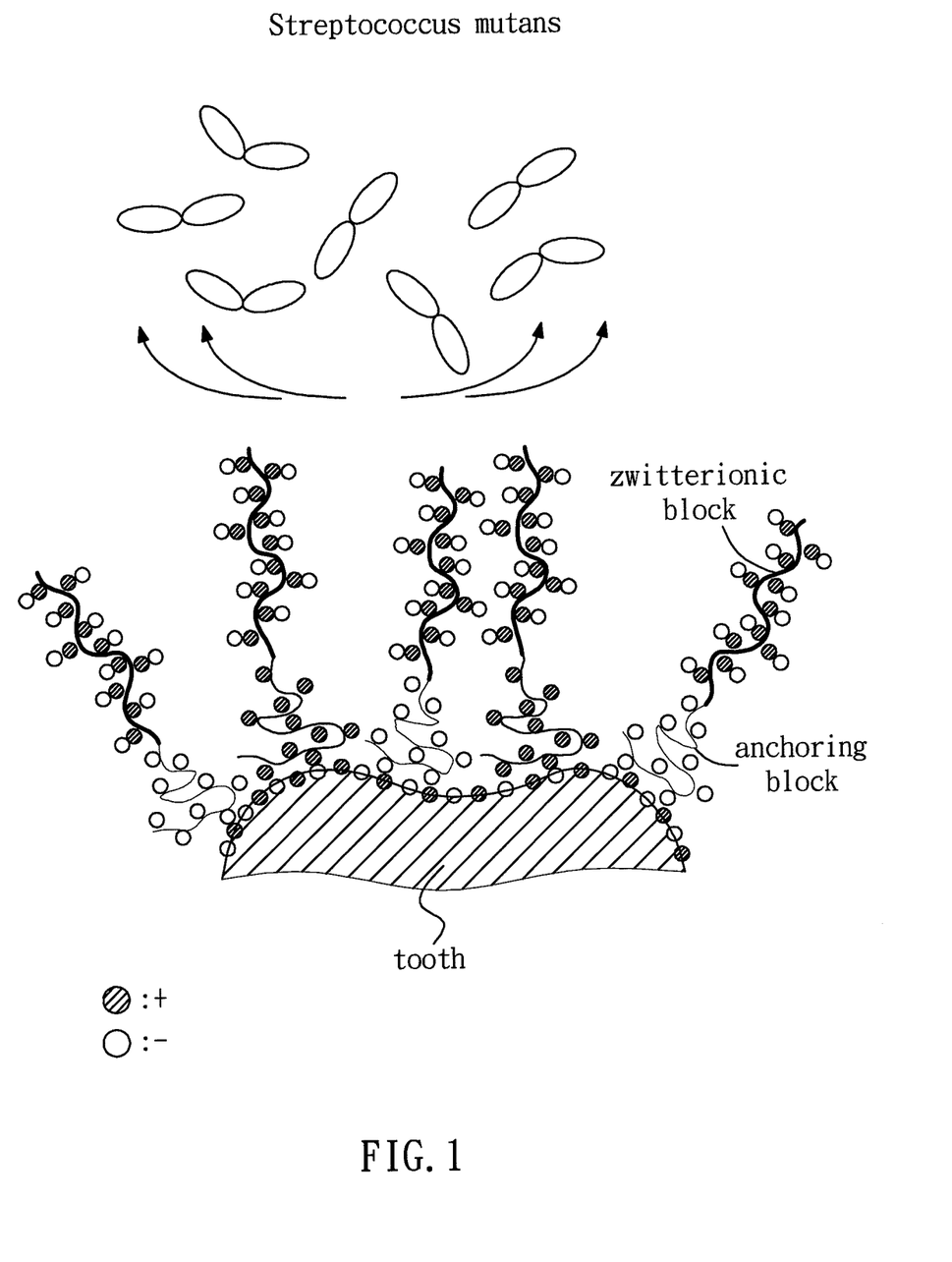
FIG. 1 illustrates the mechanism of how the bacterial resistance copolymer works on a tooth, according to an embodiment of this invention.

The bacterial resistance copolymer comprises a zwitterionic block and an anchoring block with a first electricity. In this embodiment, the first electricity can be positive electricity or negative electricity. The anchoring block is substantially formed by positively charged monomers or negatively charged monomers. The positively charged monomers are derived from the group consisting of the following:

The negatively charged monomers are derived from the group consisting of the following:

FIG. 1 illustrates the mechanism of how the bacterial resistance copolymer works on a tooth, according to the embodiment of this invention. It is believed that the surface of human teeth is naturally mix-charged. By using this feature, the anchoring block binds to tooth surfaces by electrostatic attraction, and the zwitterionic block extends outwardly to reduce the attachment of bacteria including *streptococcus mutans* to tooth surface. Notice that the potential mechanism is set forth as theory, and the present invention may be carried out without being bound to theory.

The zwitterionic block of this invention is polymerized by a zwitterionic monomer selected from the group consisting of sulfobetaine, carboxylbetaine, derivatives thereof, and combinations thereof. In an embodiment, the zwitterionic monomers are derived from the group consisting of the following:

where $R_1$, $R_2$, $R_3$, $R_4$, and $R_5$ are alkyl groups and n, m are integers of 2~5. In another embodiment, the zwitterionic block is polymerized by a zwitterionic unit comprising mix-charged monomers, and the mix-charged monomers comprise mixing two oppositely charged compounds with overall charge neutrality.

Preferably, the weight average molecular weight ($M_w$) of the block copolymer is equal to or more than 15 kDa, and the weight average molecular weight ($M_w$) of the zwitterionic block is equal to or more than 10 kDa. The dental care products of this invention may be dentifrice, toothpaste, tooth powder, mouthwash, pro-rinse, or denture cleaning agent, and preferably a liquid mouthwash. The dental care products of the present invention may also be formulated as powders, gels, foams, pastes, chewing gum, liquid concentrate, or tablets, using standard formulations known in the art, if required. In case of being formulated as a tablet, it may be dissolved in water by the user immediately prior to use.

Another embodiment of the present invention provides a dental care product with two-part formulations comprising a first agent and a second agent. Both agents may have same compositions as mentioned in the above embodiment, except that the anchoring block of one agent is positively charged, i.e., with a positive electricity, and the anchoring block of the other agent is negatively charged, i.e., with a negative electricity.

The first agent and the second agent may be stored in two separating containers for being used in sequence. The order of using these two agents may be suggested or not. In the two above-mentioned embodiments, the dental care product with two-part formulations has higher degree of bacterial resistance than that of one agent formulation.

The copolymers used in this invention are preferably a block copolymer, such as diblock copolymer (as illustrated in FIG. 1), triblock copolymer, multiblock copolymer, starblock copolymer, and graft block copolymer. It may be other forms of copolymer, such as random copolymer, branched polymer, and gradient copolymer. Examples of other forms of copolymer are illustrated in the foregoing U.S. Application entitled "Surface anti-biomolecule agent." The entire contents of which is incorporated herein by reference. By using same mechanism shown in FIG. 1, a dental care product employing the above-mentioned copolymers is believed to achieve high degree bacterial resistance as well.

In embodiments of this invention, the carrier for the active ingredients is an aqueous medium. The aqueous medium may be water, a water-surfactant mixture, a water-solvent-surfactant mixture, and the likes. The carrier used in dental care products of this invention may be alcohol-free. Surfactants may be included to solubilize some ingredients such as flavoring oils. Any food grade surfactants ascertainable to one skilled in the art may be employed by embodiments of the present invention. Preferably, the surfactant used in the dental care products of the present invention is a non-ionic surfactant in an amount sufficient to solubilize the ingredients.

The dental care products of above embodiments provide high bacterial resistance without using any essential oils or antimicrobial agents. Although not necessary, it is possible to employ essential oils or antimicrobial agents in the dental care products of this invention. Exemplary antimicrobial agents include triclosan, cetyl pyridium chloride, domiphen bromide, quaternary ammonium salts, zinc compounds, sanguinanine soluble pyrophosphates, fluorides, alexidine, octonidine, EDTA, and the likes.

The dental care products of this invention may contain other formulating agents such as flavouring agents, sweetening agents, colouring agents, thickening agents, humectants, softeners, and preservatives as those conventionally used in the oral hygiene composition art if required and which are compatible with active ingredients of this invention. The formulating agents employed by this invention will vary depending upon the particular purposes and desired functions. Those skilled in the art can select and customize these types of ingredients to provide the desired results.

Examples

Table 1 lists characteristics of nine prepared bacterial resistance copolymers, according to embodiments of the present invention. The nine prepared copolymers are divided into three groups: (1) block copolymer with a zwitterionic block and a hydrophobic block (as the anchoring block), as poly(propylene oxide)-block-poly(sulfobetaine methacrylate) (PPO-b-PSBMA); (2) block copolymer with a zwitterionic block and a positively-charged anchoring block, as poly(2-(Methacryloyloxy)ethyl]trimethylammonium)-block-poly(sulfobetaine methacrylate) (PTMA-b-PSBMA); (3) block copolymer with a zwitterionic block and a negatively-charged anchoring block, as poly(3-Sulfopropyl methacrylate potassium salt)-block-poly(sulfobetaine methacrylate) (PSA-b-PSBMA). The nine copolymers were synthesized, but not limited, using atom transfer radical polymerization (ATRP) and variant repeated units of the zwitterionic block and the anchoring block.

TABLE 1

| | Characterization of copolymers | | | | | | Average number of repeated units | | Zeta potential | Hydrodynamic size |
|---|---|---|---|---|---|---|---|---|---|---|
| | | | $M_w$ of | | polySBMA content | | | | | |
| | $M_w$ | | | $M_w$ of | | | | | | |
| Sample ID | (g/mol) | $M_w/M_n$ | poly | polySBMA | (wt %) | (mol %) | m | n | 1 mg/ml | 1 mg/ml |
| $PPO_{20}$-b-$PSBMA_{10}$ | 3952 | 1.267 | 1057 | 2895 | 73.3 | 33.3 | 20 | 10 | −0.2 | ~10 |
| $PPO_{20}$-b-$PSBMA_{20}$ | 6038 | 1.217 | 1057 | 4981 | 82.5 | 47.4 | 20 | 18 | −0.5 | ~10 |
| $PPO_{20}$-b-$PSBMA_{40}$ | 12775 | 1.236 | 1057 | 11718 | 91.7 | 67.7 | 20 | 42 | +0.7 | ~11 |
| $PTMA_{20}$-b-$PSBMA_{10}$ | 7765 | 1.214 | 4596 | 3169 | 40.8 | 33.3 | 22 | 11 | +1.4 | ~10 |
| $PTMA_{20}$-b-$PSBMA_{20}$ | 10176 | 1.435 | 4596 | 5592 | 55.0 | 47.6 | 22 | 20 | +3.2 | ~10 |
| $PTMA_{20}$-b-$PSBMA_{40}$ | 16158 | 1.312 | 4596 | 11562 | 71.6 | 65.1 | 22 | 41 | +4.3 | ~13 |
| $PSA_{20}$-b-$PSBMA_{10}$ | 7750 | 1.207 | 5060 | 2690 | 34.7 | 32.3 | 21 | 10 | −0.9 | ~10 |
| $PSA_{20}$-b-$PSBMA_{20}$ | 10620 | 1.346 | 5060 | 5660 | 53.3 | 48.8 | 21 | 20 | −2.8 | ~11 |
| $PSA_{20}$-b-$PSBMA_{40}$ | 15202 | 1.287 | 5060 | 10142 | 66.7 | 63.2 | 21 | 36 | −3.7 | ~12 |

Figure 2:
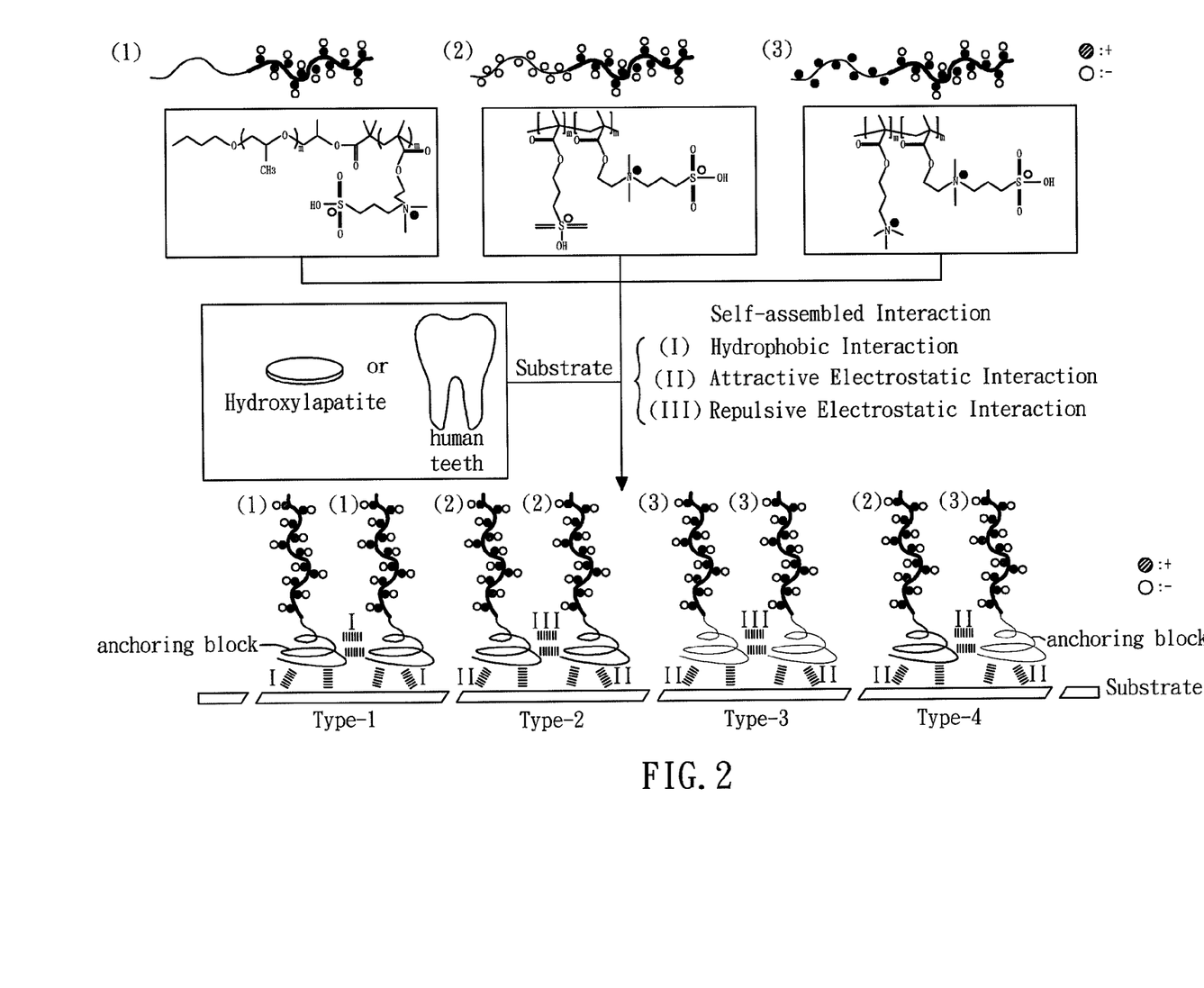
FIG. 2 shows a test scheme of in-vitro studies of nine copolymers prepared by embodiments of the present invention.

FIG. 2 shows a test scheme of in-vitro studies of the above-mentioned nine copolymers. Hydroxylapatite discs or human teeth are immersed in prepared solutions respectively containing a copolymer listed in table 1, and the bacterial resistances are respectively investigated. In detail, the prepared solutions are divided into four types: types 1-3 solutions are single agent solutions respectively employing PPO-b-PSBMA (1), PTMA-b-PSBMA (2), and PSA-b-PSBMA (3) as the active ingredient; and type 4 is a two-part formulation containing two agents, which respectively employ PTMA-b-PSBMA (2) and PSA-b-PSBMA (3) as the active ingredient, when use, a hydroxylapatite disc or human tooth is firstly immersed in one agent and then immersed in the other in a predetermined order. The scheme also shows that the prepared copolymers bind to the surface of hydroxylapatite discs or human teeth in a self-assembled manner, via hydrophobic interaction or electrostatic attractive interaction. Because types 1-3 are single agent solution, electrostatic repulsive interaction or hydrophobic interaction may be presented between their anchoring blocks. In contrast, for type 4, electrostatic attractive interactions exist between anchoring blocks after both agents are coated on the surface.

Figure 3:
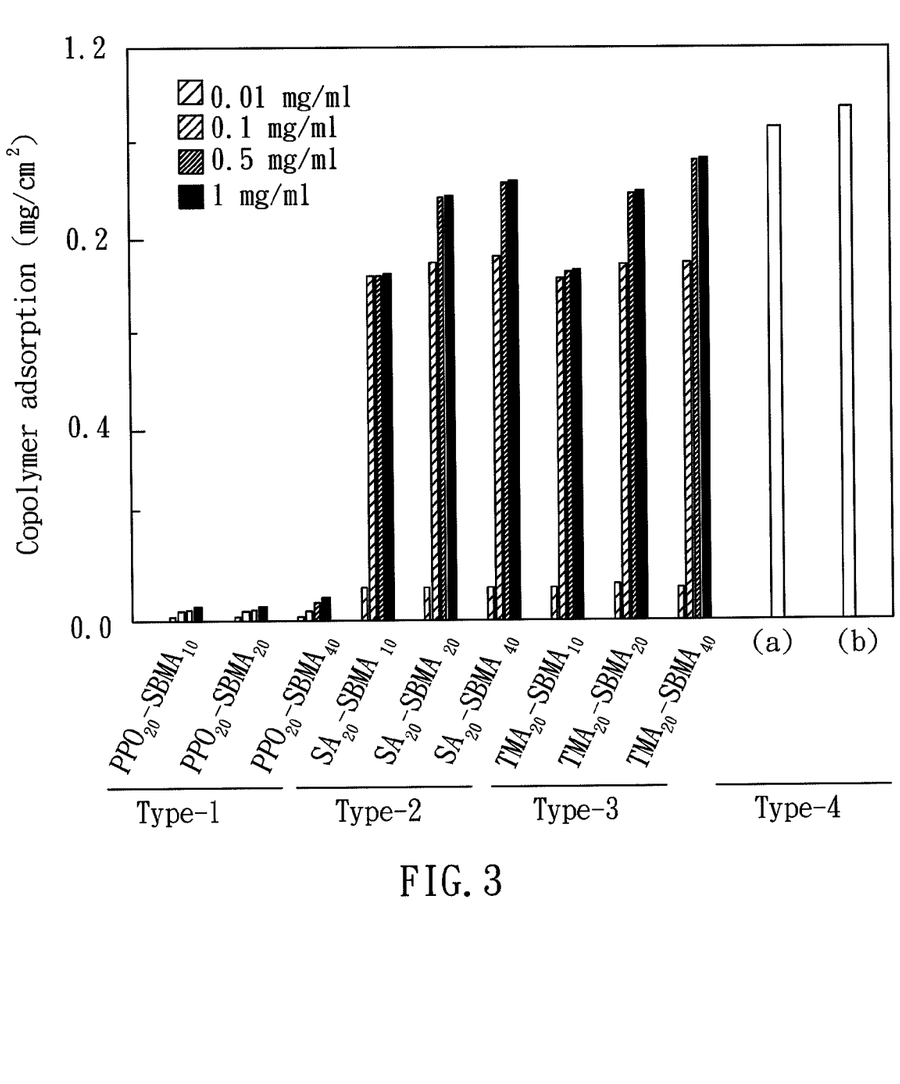
FIG. 3 shows binding capacity test of four types of solutions prepared by embodiments of the present invention.

FIG. 3 shows binding capacity test of prepared four types of solutions. For type 1-3 dental care solutions, nine prepared bacterial resistance copolymers are respectively dissolved in phosphate buffer saline (PBS) with different concentrations from 0.01 mg/ml to 1 mg/ml, and then hydroxylapatite discs are respectively immersed into the prepared solutions for checking the binding capacity. Higher copolymer adsorption (mg/cm$^2$) indicates higher binding capacity of the bacterial resistance copolymer. For type 4 dental care solution, PSA$_{20}$-b-PSBMA$_{40}$ and PTMA$_{20}$-b-PSBMA$_{40}$ are respectively dissolved in PBS with concentration of 1 mg/ml as two agents of the two-part formulations. Sample (a) denotes a hydroxylapatite disc firstly coated with agent containing PSA$_{20}$-b-PSBMA$_{40}$ and then coated with agent containing PTMA$_{20}$-b-PSBMA$_{40}$, and sample (b) denotes another hydroxylapatite disc coated the two agents in sequence in reverse order to sample (a).

As shown in FIG. 3, type-1 solution reveals poor binding capacity to surface of hydroxylapatite disc, type-2 and type-3 solutions reveal good binding capacity except the lowest concentration ones (0.01 mg/ml), and type-4 solutions reveal excellent binding capacity regardless of the coating order.

Figure 4:
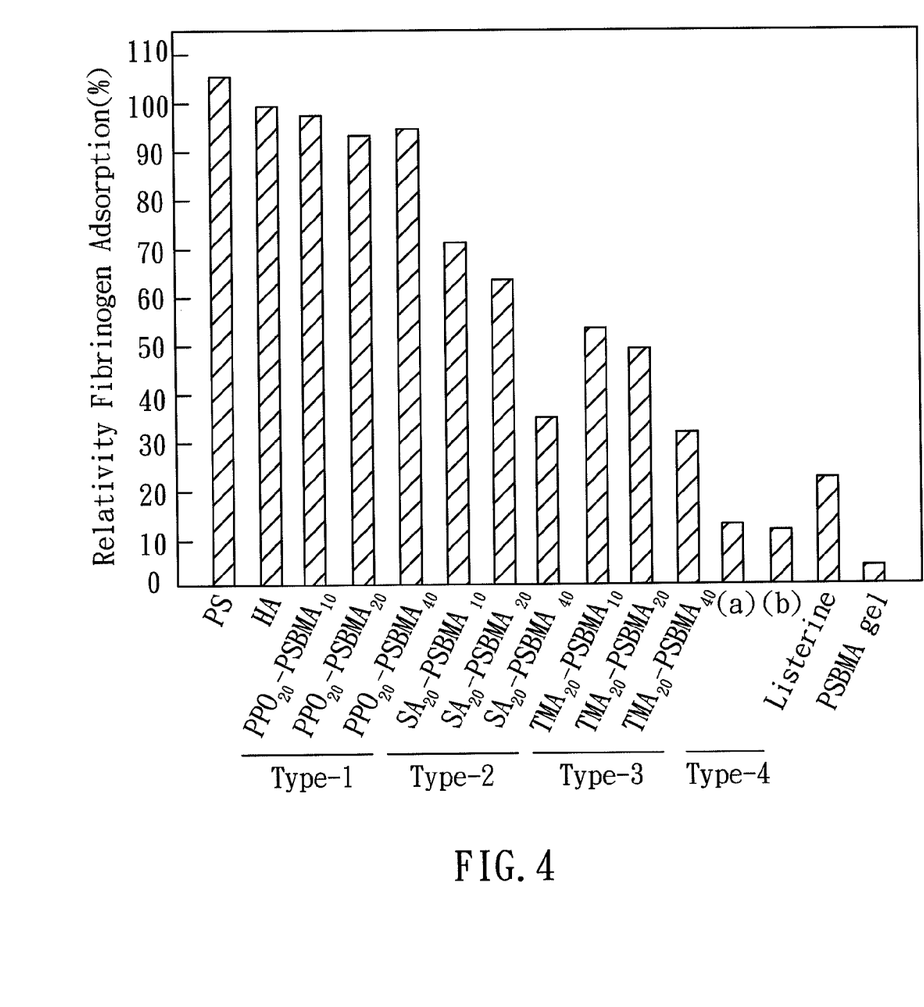
FIG. 4 shows single protein adsorption test of four types of solution prepared by embodiments of the present invention.
Figure 5A:
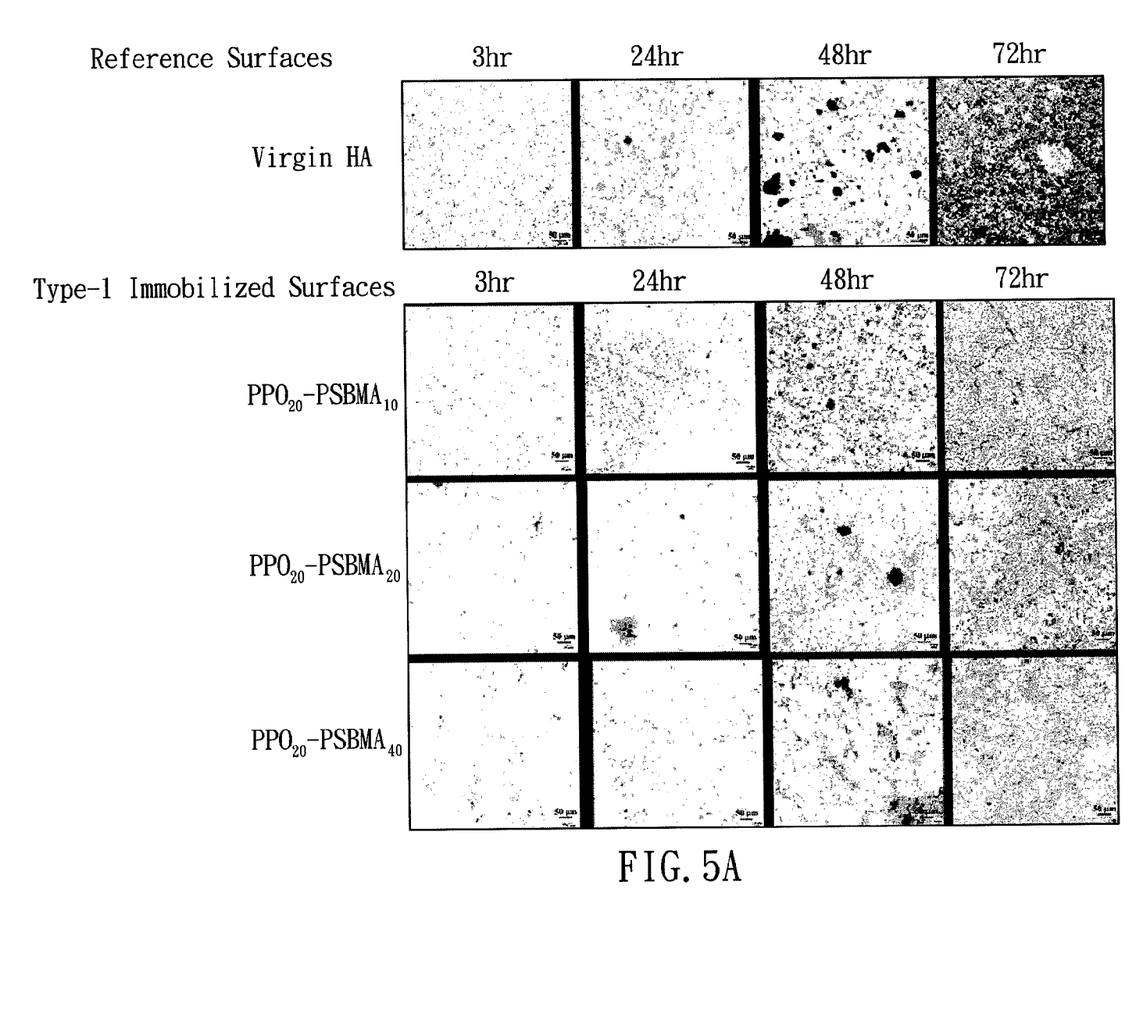
FIGS. 5A-5E show images of the bacteria coverage test of hydroxylapatite discs coated with dental care solutions of embodiments of this invention.
Figure 5B:
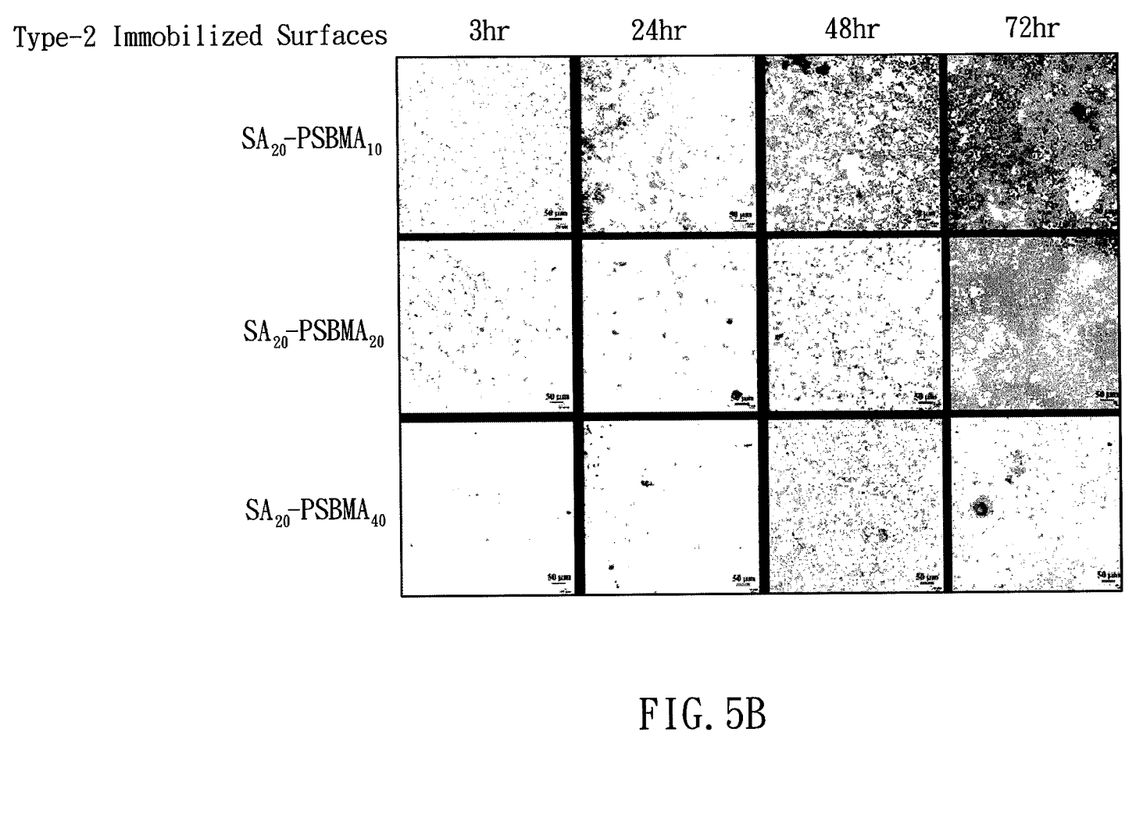
Figure 5C:
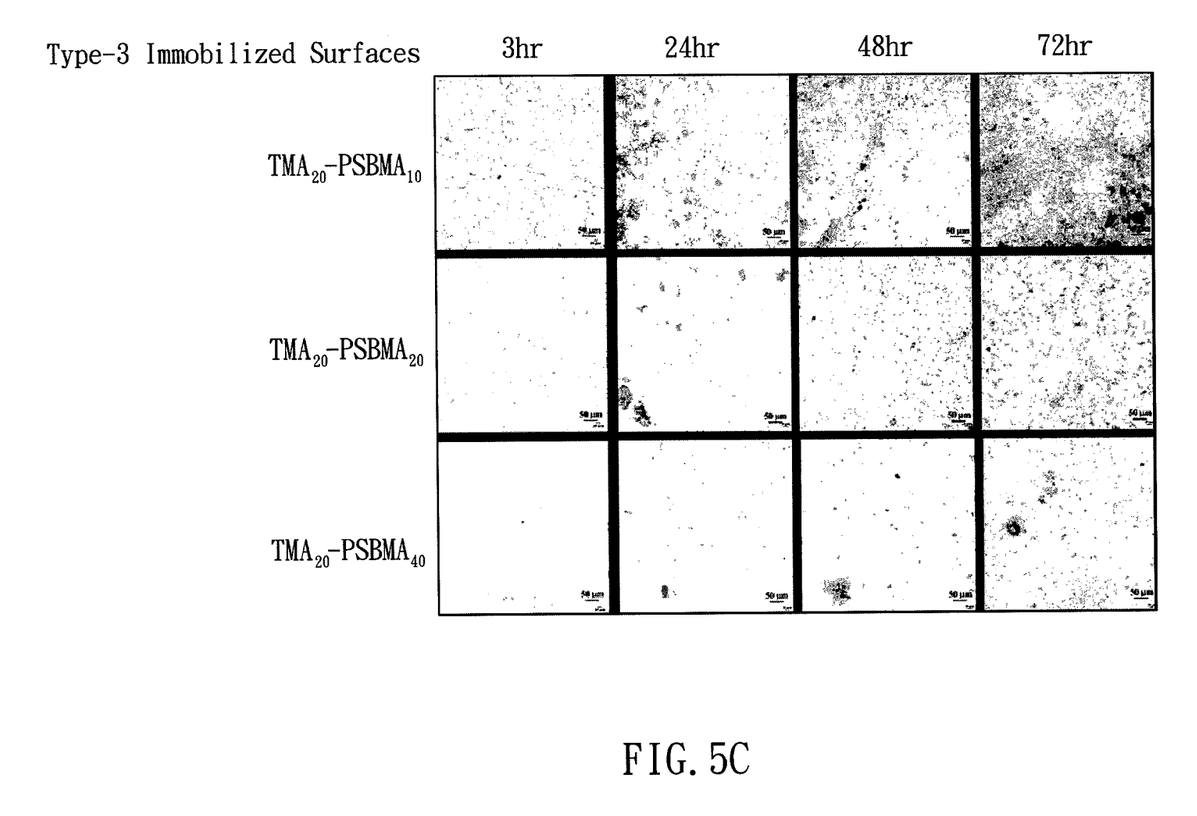
Figure 5D:
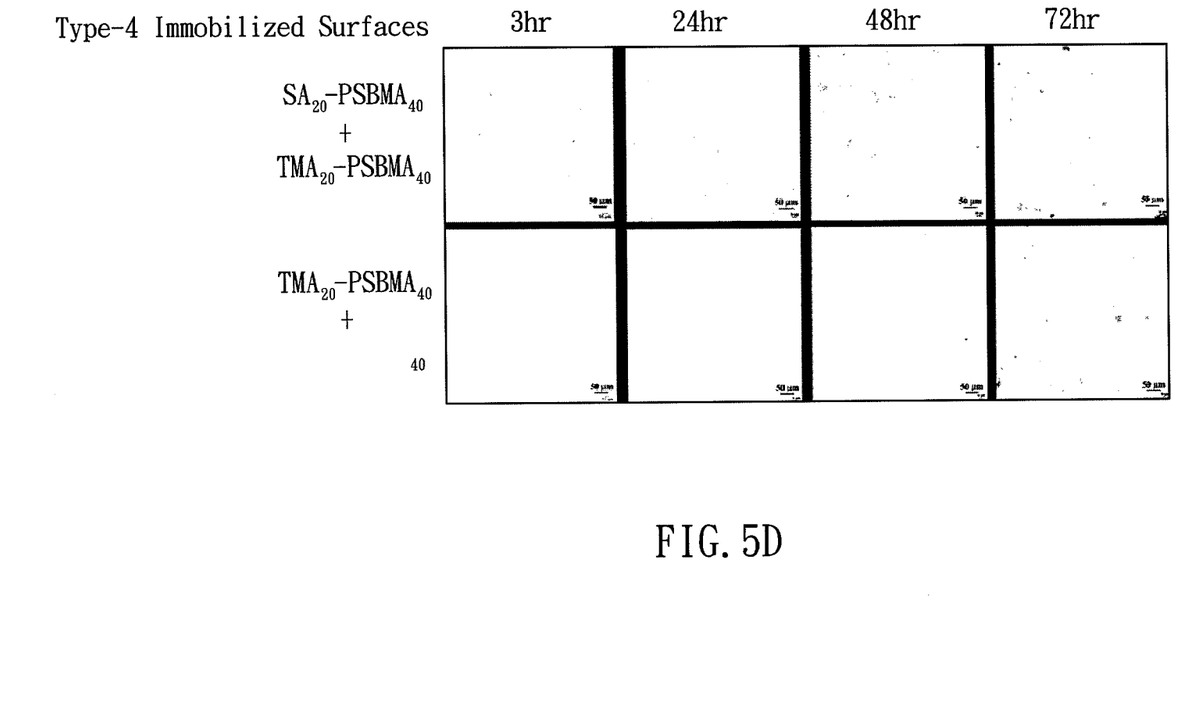
Figure 5E:
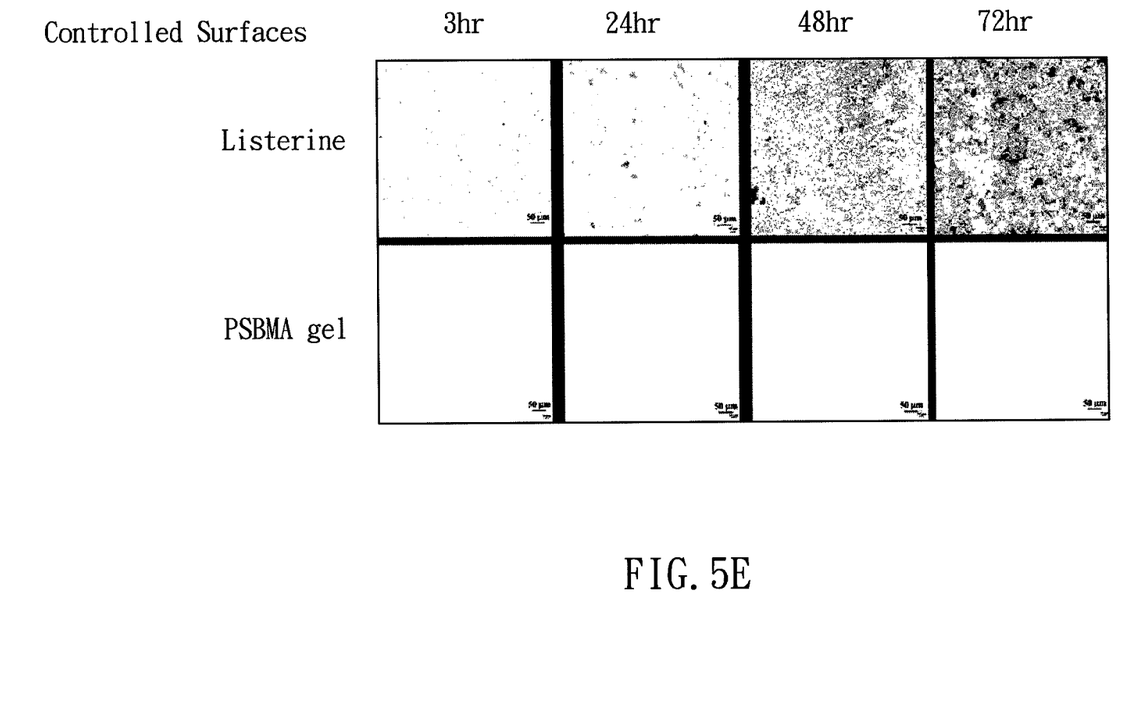

It is believed that proteins deposit on surface of tooth will assist the oral bacteria leading to various dental caries. Thus a dental care product should provide excellent resistance against proteins. FIG. 4 shows single protein adsorption test of prepared four types of solution and some comparative samples including polystyrene (PS), hydroxylapatite disc (HA), Listerine® mouthwash, and PSBMA gel. The four types of solution are prepared as mentioned above, except that the concentrations of the copolymers are fixed at 1 mg/ml.

Hydroxylapatite discs are respectively immersed in each sample solution for coating the copolymers or active ingredient on their surface, and then contacted with single protein solution of fibrinogen to evaluate the protein resistance. All data are normalized to the data of virgin HA, i.e., fibrinogen absorbed by virgin HA without coating copolymers or active ingredient on its surface. The results show that hydroxylapatite discs treated by Type-1 solutions adsorb fibrinogen comparable to virgin HA, hydroxylapatite discs treated by Type-2 solutions reveal acceptable protein resistance, and hydroxylapatite discs treated by Type-3 solutions reveal superior protein resistance than Listerine® mouthwash.

Figure 6:
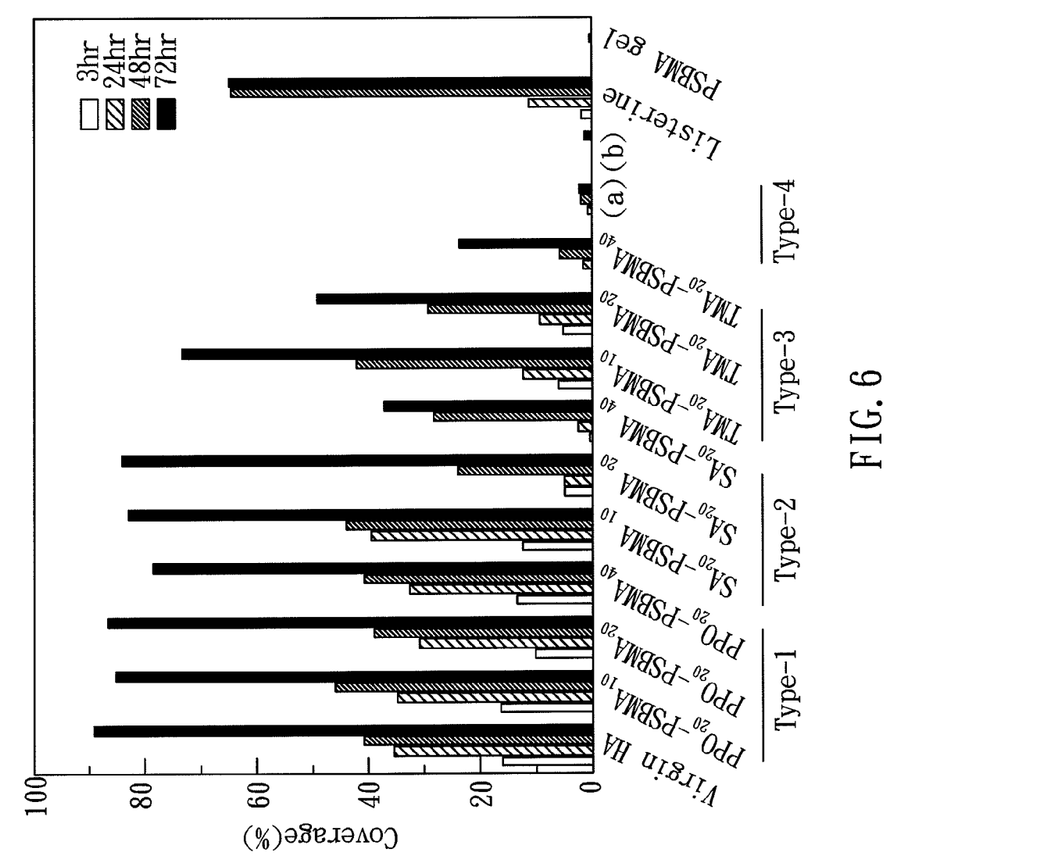
FIG. 6 shows numerical data of FIG. 5A-5E.

FIGS. 5A-5E and FIG. 6 show bacteria coverage test of prepared four types of solution and some comparative samples including virgin hydroxylapatite disc (HA), Listerine® mouthwash, and PSBMA gel, where FIG. 5 shows images of the bacteria coverage test, and FIG. 6 shows numerical data of FIG. 5A-5E. Hydroxylapatite discs are respectively treated by type-1, type-2, type-3, type-4, Listerine® mouthwash, and PSBMA gel using the same method mentioned above, and then contacted with human saliva up to 72 hours to evaluate their bacterial resistance. Human saliva containing *streptococcus mutans* forms biofilms on surfaces of the hydroxylapatite discs. The biofilm coverage percentage is used to evaluate the bacterial resistance. Images and corresponding numerical data are taken and calculated at times 3rd, 24th, 48th, and 72nd hour, respectively. All steps are performed under physiological conditions.

Images of biofilm of the virgin hydroxylapatite disc, without being treated with any active ingredient, are used as reference surfaces, where green flecks or areas represent the biofilm. Compared to virgin HA, all type-1 solutions reveal small bacterial resistance no matter whatever molecular weight. Type-2 solutions reveal good bacterial resistance at times 3rd hour and 24th hour, except the PSA$_{20}$-b-PSBMA$_{10}$ case. This indicates that for this type of dental care product, the molecular weight of the zwitterionic block, e.g., PSBMA, should be approximate to or more than that of the anchoring block, e.g., PSA. Type-3 solutions reveal a bit higher bacterial resistance than type-2 solutions. All three samples of type-3 reveal good bacterial resistance at times 3rd hour and 24th hour. It is also observed that samples with higher molecular weight of PSBMA have higher bacterial resistance. Type-4 solutions reveal excellent bacterial resistance, and sample (b) is better than sample (a). For sample (a), no biofilm is founded at the 3rd hours, and the bacterial coverage at 72nd hours is less than 3%; for sample (b), no biofilm is founded up to 48th hours, and only a little is founded at 72nd hours. For commercial Listerine® mouthwash, a little bacterial coverage is founded at 3 hours, about 10% bacterial coverage founded at 24th hours, about 60% bacterial coverage founded at 48 hours.

Figure 7:
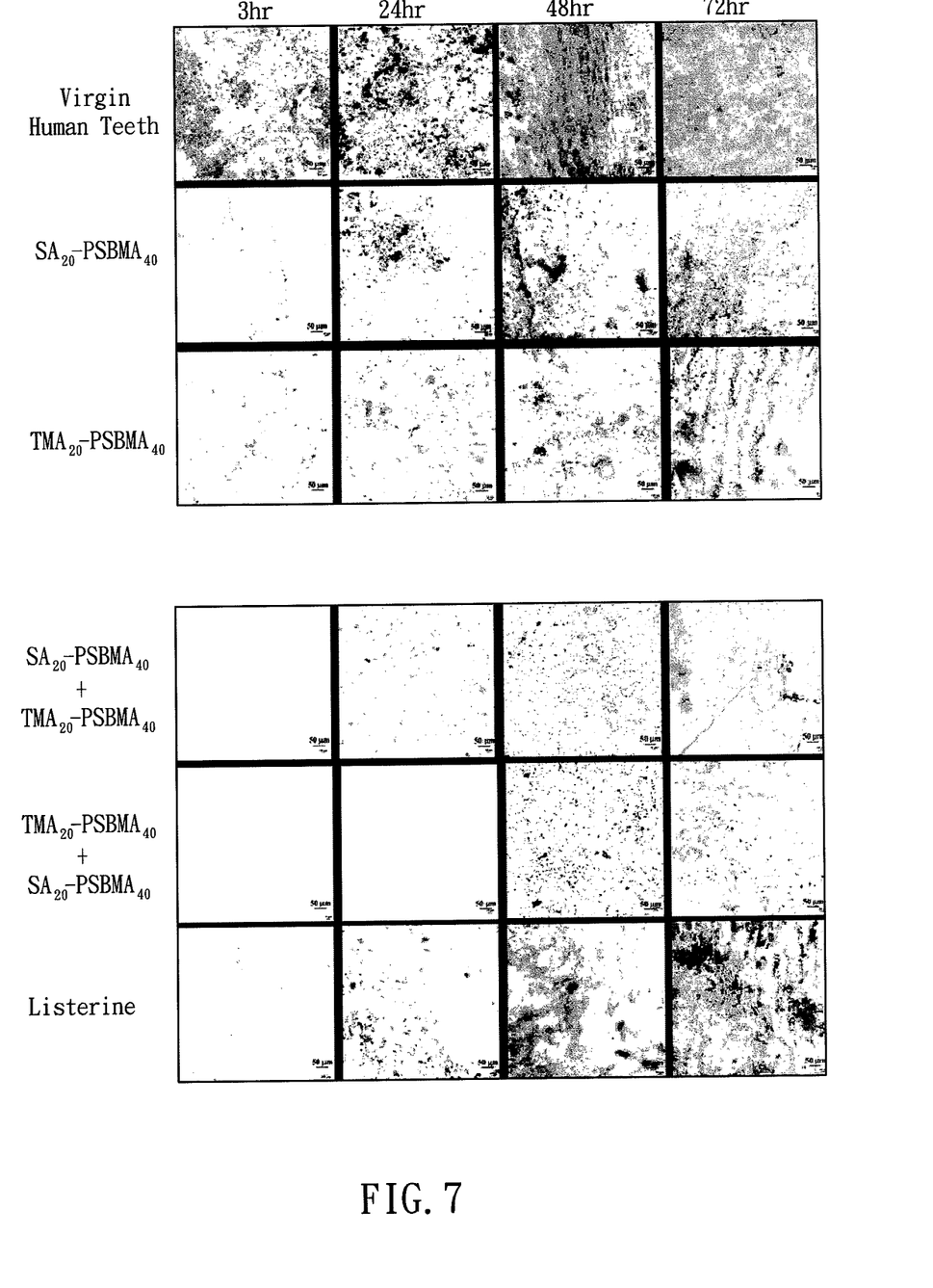
FIG. 7 shows images of the bacteria coverage test of human teeth coated with dental care solutions of embodiments of this invention.
Figure 8:
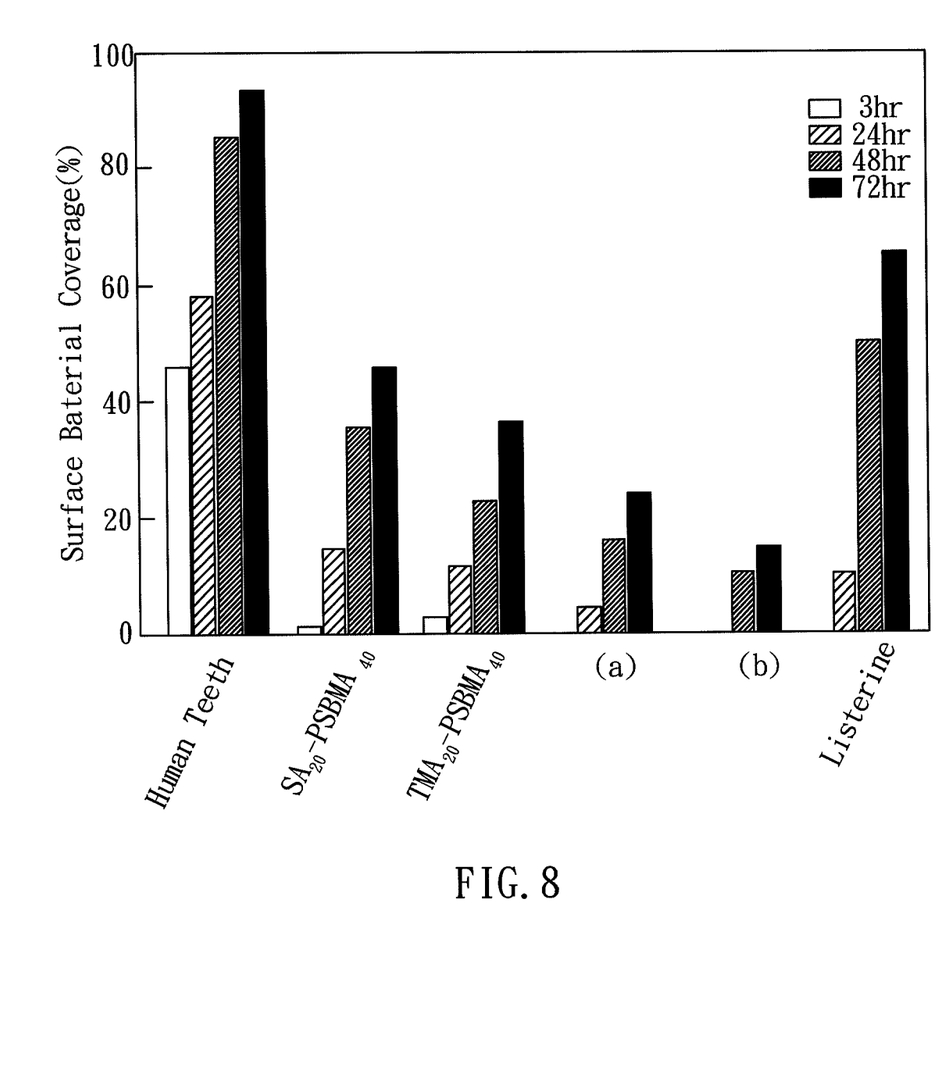
FIG. 8 shows numerical data of FIG. 7.

FIG. 7 and FIG. 8 show bacteria coverage test similar to FIGS. 5A-5E and FIG. 6, except the only difference that this test is performed on human teeth rather than hydroxylapatite discs. FIG. 7 shows images of the bacteria coverage test, and FIG. 8 shows numerical data of FIG. 7. Because human teeth are difficult to obtain, only one sample is selected to test for type-2 and type-3 solutions, and type-1 solutions are untested. Again, images of biofilm of the virgin human teeth, without being treated with any active ingredient, are used as reference surfaces.

As shown in FIG. 7 and FIG. 8, sample solutions containing PSA$_{20}$-b-PSBMA$_{40}$ or PTMA$_{20}$-b-PSBMA$_{40}$ reveal good bacterial resistance comparable to Listerine® mouthwash, and both two samples of the type-4 solutions reveal excellent bacterial resistance superior than Listerine® mouthwash.

The data show that the dental care products of this invention are able to resist bacteria at levels comparable to, or superior than, the commercial products such as Listerine® mouthwash.

Although specific embodiments have been illustrated and described, it will be appreciated by those skilled in the art that various modifications may be made without departing from the scope of the present invention, which is intended to be limited solely by the appended claims.

What is claimed is:

1. A dental care product with two-part formulations, said dental care product with two-part formulations consisting of: (a) a first agent comprising an orally acceptable carrier and equal to or more than 0.1 mg/ml of a block copolymer containing an negatively charged anchoring block and a zwitterionic block; and (b) a second agent comprising an orally acceptable carrier and equal to or more than 0.1 mg/ml of another block copolymer containing an positively charged anchoring block and a zwitterionic block.

2. The dental care product with two-part formulations according to claim 1, wherein the negatively charged anchoring block is polymerized from a monomer selected from the group consisting of following:

3. The dental care product with two-part formulations according to claim 1, wherein the positively charged anchoring block is polymerized from a monomer selected from the group consisting of following:

4. The dental care product with two-part formulations according to claim 1, wherein the zwitterionic block is polymerized from a monomer selected from the group consisting of following:

where R1, R2, R3, R4, and R5 are alkyl groups and n, m are integers of 2~5.

5. The dental care product with two-part formulations according to claim 1, wherein the block copolymer containing an negatively charged anchoring block and a zwitterionic block is poly(3-Sulfopropyl methacrylate potassium salt)-block-poly(sulfobetaine methacrylate) (PSA-b-PSBMA).

6. The dental care product with two-part formulations according to claim 1, wherein the block copolymer containing an positively charged anchoring block and a zwitterionic block is poly(2-(Methacryloyloxy)ethyl]trimethylammonium)-block-poly(sulfobetaine methacrylate) (PTMA-b-PSBMA).

7. The dental care product with two-part formulations according to claim 5, wherein the weight average molecular weight (Mw) of the poly(3-Sulfopropyl methacrylate potassium salt)-block-poly(sulfobetaine methacrylate) (PSA-b-PSBMA) is equal to or more than 15 kDa.

8. The dental care product with two-part formulations according to claim 6, wherein the weight average molecular weight (Mw) of poly(2-(Methacryloyloxy)ethyl]trimethylammonium)-block-poly(sulfobetaine methacrylate) (PTMA-b-PSBMA) is equal to or more than 15 kDa.

9. The dental care product with two-part formulations according to claim 4, wherein the zwitterionic block is poly(sulfobetaine methacrylate).

10. The dental care product with two-part formulations according to claim 9, wherein the weight average molecular weight (Mw) of the poly(sulfobetaine methacrylate) is equal to or more than 10 kDa.

11. A method for reducing the attachment of biomolecules onto surfaces, said method comprising: applying a two-part formulation onto the surfaces selected from the group consisting of teeth and hydroxylapatite discs, wherein the two-part formulation consisting of (a) a first agent comprising an orally acceptable carrier and equal to or more than 0.1 mg/ml of poly(3-Sulfopropyl methacrylate potassium salt)-block-poly(sulfobetaine methacrylate) (PSA-b-PSBMA); and (b) a second agent comprising an orally acceptable carrier and equal to or more than 0.1 mg/ml of poly(2-(Methacryloyloxy)ethyl]trimethylammonium)-block-poly(sulfobetaine methacrylate) (PTMA-b-PSBMA).

12. The method according to claim 11, wherein the weight average molecular weight (Mw) of the poly(3-Sulfopropyl methacrylate potassium salt)-block-poly(sulfobetaine methacrylate) (PSA-b-PSBMA) is equal to or more than 15 kDa.

13. The method according to claim 11, wherein the weight average molecular weight (Mw) of poly(2-(Methacryloyloxy)ethyl]trimethylammonium)-block-poly(sulfobetaine methacrylate) (PTMA-b-PSBMA) is equal to or more than 15 kDa.

14. The method according to claim 11, wherein the weight average molecular weight (Mw) of the poly(sulfobetaine methacrylate) is equal to or more than 10 kDa.

15. The method according to claim 11, wherein the two-part formulation being all or a part of dentifrice, toothpaste, tooth powder, mouth wash, pro-rinse, and denture cleaning agent.

* * * * *